United States Patent
Omata et al.

(10) Patent No.: US 7,615,014 B2
(45) Date of Patent: Nov. 10, 2009

(54) DEVICE FOR MEASURING ELASTIC PROPERTIES OF TISSUE

(75) Inventors: Sadao Omata, Tokyo (JP); Chris E. Constantinou, Stanford, CA (US); Osamu Yamaguchi, Fukushima (JP); Hideyuki Usui, Koriyama (JP)

(73) Assignee: Nihon University, Tokyo (JP)

( * ) Notice: Subject to any disclaimer, the term of this patent is extended or adjusted under 35 U.S.C. 154(b) by 278 days.

(21) Appl. No.: 10/545,236

(22) PCT Filed: Feb. 10, 2004

(86) PCT No.: PCT/JP2004/001372

§ 371 (c)(1),
(2), (4) Date: Aug. 12, 2005

(87) PCT Pub. No.: WO2004/071288

PCT Pub. Date: Aug. 26, 2004

(65) Prior Publication Data

US 2006/0064038 A1    Mar. 23, 2006

(30) Foreign Application Priority Data

Feb. 12, 2003    (JP)    ............... 2003-034301

(51) Int. Cl.
A61B 5/103    (2006.01)
(52) U.S. Cl. .............. 600/587; 600/591; 600/593
(58) Field of Classification Search ............ 600/591, 600/592, 593, 587
See application file for complete search history.

(56) References Cited

U.S. PATENT DOCUMENTS 5,153,916 A * 10/1992 Inagaki et al. ............. 382/151

(Continued)

FOREIGN PATENT DOCUMENTS

JP    Y2 1-22645    7/1989

(Continued)

OTHER PUBLICATIONS

"Evlauation of the Soft Tissue Elasticity with Forced Vibration by Ultrasonic Pulsed Dopplar Method" by Kino Tooru and Honda Satoshi in Transactionso f the Society of Instrument and Control Engineers vol. 35 No. 3 p. 305-311 (1999).*

(Continued)

*Primary Examiner*—Max Hindenburg
*Assistant Examiner*—Michael C Stout
(74) *Attorney, Agent, or Firm*—Oliff & Berridge, PLC

(57) ABSTRACT

A device for measuring elastic properties, comprising a long bar-like probe base (42) and probes (50a, 50c) fitted to the probe base (42) driven as to be pressed against and withdrawn from a living body tissue. The probes are so formed that generally semi-spherical contact balls (58) having stress detection bases (56) are fitted to the ends of leaf strings (52) and stress detection sensors (60) are disposed on the stress detection bases (56). Light-receiving elements are fitted to the opposite side of the leaf displacement sensors (62a, 62b). The stress sensors (60) and displacement sensors (62a, 62b) are connected to the device body through signal lines (92, 94), respectively. The profile of the displacement of the tissue is calculated and displayed in a manner indicating correlation with stress.

12 Claims, 13 Drawing Sheets

U.S. PATENT DOCUMENTS

| | | | |
|---|---|---|---|
| 5,316,016 A * | 5/1994 | Adams et al. | 600/587 |
| 5,396,887 A * | 3/1995 | Imran | 600/374 |
| 5,684,801 A * | 11/1997 | Amitay et al. | 370/447 |
| 5,766,137 A * | 6/1998 | Omata | 600/587 |
| 5,833,605 A * | 11/1998 | Shah | 600/393 |
| 5,858,556 A * | 1/1999 | Eckert et al. | 428/586 |
| 6,081,737 A * | 6/2000 | Shah | 600/393 |
| 6,142,959 A * | 11/2000 | Sarvazyan et al. | 600/587 |
| 6,352,507 B1 * | 3/2002 | Torp et al. | 600/438 |
| 6,748,255 B2 * | 6/2004 | Fuimaono et al. | 600/374 |
| 6,890,307 B2 * | 5/2005 | Kokate et al. | 600/549 |
| 7,077,812 B2 * | 7/2006 | Naghavi | 600/587 |
| 2002/0111560 A1 * | 8/2002 | Kokate et al. | 600/549 |
| 2003/0187370 A1 * | 10/2003 | Kodama | 600/591 |
| 2005/0124920 A1 * | 6/2005 | Gregersen | 600/593 |

FOREIGN PATENT DOCUMENTS

| | | |
|---|---|---|
| JP | B2 3-54575 | 8/1991 |
| JP | B2 4-19862 | 3/1992 |
| JP | B2-3151153 | 1/2001 |
| WO | WO 03/063698 A1 | 8/2003 |

OTHER PUBLICATIONS

"3D Imaging Interpolation Based on Direction Coherence," by Yongmei Wang, Zhunping Zang, and Baining Guo in Mathematical Methods in Biomedical Image Analysis, 2001. MMBIA 2001. IEEE Workshop on Dec. 9-10, 2001 pp. 195-202.*

* cited by examiner

DEVICE FOR MEASURING ELASTIC PROPERTIES OF TISSUE

TECHNICAL FIELD

The present invention relates to a device for measuring elastic properties of a living tissue.

BACKGROUND ART

Women who have delivered children or of an advanced age are more likely to suffer urinary incontinence because childbearing and age can cause muscles supporting the urethra to become over stretched and their elasticity to decrease. In some afflicted patients, an operation is performed to recover the elasticity of the muscle supporting the urethra by, for example, providing a support hole on a pelvis through which the muscle surrounding the urethra are lifted up. In addition to, or in combination with, such an operation, training for recovering the elasticity of the muscle surrounding the urethra can be provided.

For carrying out the operation properly, it is necessary to determine an extent of reduction in elasticity with respect to the muscle around the urethra and to define the degree of lifting up the muscle through the support hole suitable for recovery of the elasticity. In addition, it is also important to evaluate the degree of elasticity recovery after the operation. Still further, when the elasticity recovery training is provided, it is also necessary to evaluate the extent of elasticity reduction for the muscle surrounding the urethra and the effective recovery achieved by the training. Evaluation of the elasticity of the muscles surrounding the urethra has previously been determined by diagnosis such as manual palpation, which relies heavily on the experience and skill of the person performing the examination.

Although it is theoretically possible to directly measure elastic properties of surrounding muscle tissue by inserting a probe into the urethra without employing techniques such as palpation by the operator, in practice such probe insertion imposes an undesirable burden on a patient because of the narrowness of the urethra.

In consideration of the above, evaluation of the elasticity of the muscle around the urethra through a living body tissue inside a vaginal canal by inserting a probe into the vaginal canal has been considered, because the probe can be inserted through a vagina which is located in the immediate vicinity of the urethra and has a diameter of about 15 mm. However, because one function of the muscle surrounding the urethra resides in dilatation and contraction properties which provide dilatation and contraction of the urethra by an adequate elasticity, the evaluation cannot be sufficiently conducted by a general method such as a stress measurement or a strain measurement performed with respect to the tissue inside the vaginal canal.

Further, the extent of reduction in the muscle elasticity which causes urinary incontinence can not sufficiently be evaluated by a topical measurement such as measurement at one point inside the vaginal canal. The same is true for an evaluation of elasticity recovery after operation or during training. That is, it is impossible to evaluate which part of muscle has been recovered and which part of muscle has not been recovered.

For evaluating the functions of muscles surrounding the urethra, it is preferable that the extent of dilatation and contraction of a whole vagina is observed in real time by allowing the patient to "overstrain" or "relax" their muscles for example, but means appropriate for carrying out such observations have not been conceived.

In addition, for reflecting results of the training of the patient into a next training, it is desired to use an evaluation device, by which the patient can continuously conduct the training by themselves and can easily understand the degree of recovery at home.

The present invention advantageously provides a device for measuring elastic properties of living tissue which allows for real-time measurement of dilatation and contraction properties of the living tissue, and solves the problems noted above. The present invention further advantageously provides a device for measuring elastic properties of a living tissue by which dilatation and contraction properties of the living tissue can easily be understood.

DISCLOSURE OF THE INVENTION

To achieve the above described objects, a device for measuring elastic properties of living tissue according to the present invention is a device for measuring elastic properties of a living tissue by which elastic properties of a tissue surrounding a canal of a living body is measured by inserting the device through the canal, characterized by comprising a probe base to be inserted through the canal; a plurality of probes provided around an insertion axis of the probe base and at the same insertion depth in a direction of the insertion axis the probes being placed in close vicinity to the tissue inside the canal so as to be driven in a manner being pressed against and withdrawn from a plurality of measurement positions on the tissue; a plurality of stress detection sensors provided on the respective probes, each of which detects a stress applied to the tissue at each measurement position on the basis of a reaction force from the tissue when the probe is driven so as to be pressed and withdrawn; a plurality of displacement detection sensors provided corresponding to respective stress detection sensors, each of which detects a displacement of the tissue at each measurement position on the basis of a displacement of each stress detection sensor with respect to the probe base; a displacement profile calculation part for calculating a displacement profile of the canal displaced in a manner so as to be pressed and withdrawn, based on each displacement at each measurement position and on a standard profile having no stress applied to the tissue, at the above described insertion depth into the canal; and display means for displaying a change of the displacement profile caused by the pressing and withdrawing motion and a change of each stress value corresponding to each profile in real time.

According to the above described configuration, a plurality of probes inserted through the canal are provided around the insertion axis at the same insertion depth in a direction of the insertion axis. The plurality of probes are driven so as to be pressed against and withdrawn from the plurality of measurement positions on the tissue inside the canal, and then a stress and a displacement at each measurement position are detected. Subsequently, a displacement profile produced by the pressing and withdrawing motion is calculated from a standard profile of the canal and from the displacement at each measurement position, and then displayed together with a change of stress. Therefore, it is possible to measure the dilatation and contraction properties inside the canal such as a vagina in real time. In addition, visually displaying a change of the displacement profile allows a patient to easily understand the dilatation and contraction properties of the living tissue, for example. Further, the standard profile is preferably a tomogram at the above described insertion depth into the canal.

In addition, the display means preferably displays a displacement profile and further displays graphics of a size corresponding to each value of the stress at the each measurement positions so as to be superimposed on positions corresponding to measurement position on the displacement profile. According to the above described configuration, the change of stress can be measured in real time in association with the change of displacement profile, and can be observed visually.

In addition, the displacement profile calculation part preferably calculates a displacement profile by interpolation between adjacent measurement positions, based on the each displacements at the each measurement position. According to the above described configuration, it is possible to measure in real time and observe visually not only a change in displacement at each of discrete measurement positions but also a change of an overall cross sectional view of the tissue.

In addition, each plurality of probes is further preferably provided at a plurality of insertion depths, respectively. According to the above described configuration, it is possible not only to perform measurement around an inner periphery of the canal but also to perform measurement in a depth direction of the canal.

In addition, the device for measuring elastic properties of a living tissue according to the present invention is characterized by further comprising storage means for storing displacement profiles and stress values corresponding to the profiles at respective measurement times, wherein the display means read the displacement profiles at the respective measurement times and the corresponding respective stress values from the storage means to display thereof, respectively.

According to the present invention, it is possible to display on the same screen a situation in which the displacement profile is changing every moment. In addition, it is also possible to display on the same screen a situation in which the stress is changing every moment. Further, it is possible to display on the same screen a situation in which the displacement profile and the stress change from moment to moment.

In addition, the device for measuring elastic properties of a living tissue according to the present invention preferably comprises transmission means for transmitting the displacement profiles at the respective measurement times and the respective stress values corresponding to the profiles to the outside. According to the above described configuration, the same data can be measured and observed at a plurality of locations. For example, a patient can observe the elastic properties of the living tissue at home while transmitting the date to a doctor or the like, and then can receive appropriate instructions.

In addition, a device for measuring elastic properties of living tissue according to the present invention is a device for measuring elastic properties of a living tissue by which elastic properties of a tissue surrounding a canal of a living body is measured by inserting the device through the canal, characterized by comprising a probe base to be inserted through the canal; a plurality of probes provided around an insertion axis of the probe base and at the same insertion depths in a direction of the insertion axis, the probes being placed in close vicinity to the tissue inside the canal so as to be driven in a manner being pressed against and withdrawn from a plurality of measurement positions on the tissue; a plurality of hardness sensor parts provided on respective probes; hardness detection means for detecting a hardness of the tissue at each measurement position, based on a signal from the hardness sensor part; a plurality of displacement detection sensors provided corresponding to the respective hardness sensor parts, each of which detects a displacement of the tissue at each measurement position on the basis of a displacement of each hardness sensor part with respect to the probe base; a displacement profile calculation part for calculating a displacement profile of the canal displaced in a manner so as to be pressed and withdrawn, based on each displacement at each measurement position and on a standard profile having no stress applied to the tissue, at the above described insertion depth into the canal; and display means for displaying a change of the displacement profile caused by the pressing and withdrawing motion and the corresponding change of each hardness in real time.

According to the above described configuration, hardness and displacement of the tissue can be evaluated. Because the hardness is closely related to an elastic coefficient which is a ratio of a stress to a strain, it is possible to measure and observe in real time a change associated with an elastic coefficient of the tissue from a change of hardness.

Further, a device for measuring elastic properties of a living tissue according to the present invention is characterized in that the above described hardness sensor part comprises a vibrator, a vibration detection sensor, an input terminal connected to the vibrator, and an output terminal connected to the vibration detection sensor; and the above described hardness detection means comprises an amplifier whose input terminal is connected to the output terminal of the hardness sensor part, and a phase shift circuit provided between the output terminal of the amplifier and the input terminal of the hardness sensor part so as to shift a phase difference to zero by modulating a frequency when the phase difference is produced between an input waveform to the vibrator and an output waveform from the vibration detection sensor, wherein the hardness of the tissue is detected from a change of frequency which is caused by a change in hardness of the tissue while keeping a resonant condition of a closed loop which comprises the hardness sensor part and the tissue. According to the above described configuration, a quantitative value for the hardness of the tissue can be detected.

As described above, the present invention, makes it possible to measure the dilatation and contraction properties of living tissue in real time. By using the device for measuring elastic properties of living tissue of to the present invention, dilatation and contraction properties of the living tissue can easily be understood.

BEST MODE FOR CARRYING OUT THE INVENTION

Embodiments according to the present invention will now be described in detail with reference to the drawings. Although the vagina is used as an example of a living body canal in the following description, the invention is obviously applicable to body canals other than the vagina such as, for example, the pharynx, the anal canal, the colon, or an auditory tube. And the shape, size, or structure of a tip portion of a probe part may be easily modified for applications involving living body cavities, such as the heart or stomach.

Figure 1:
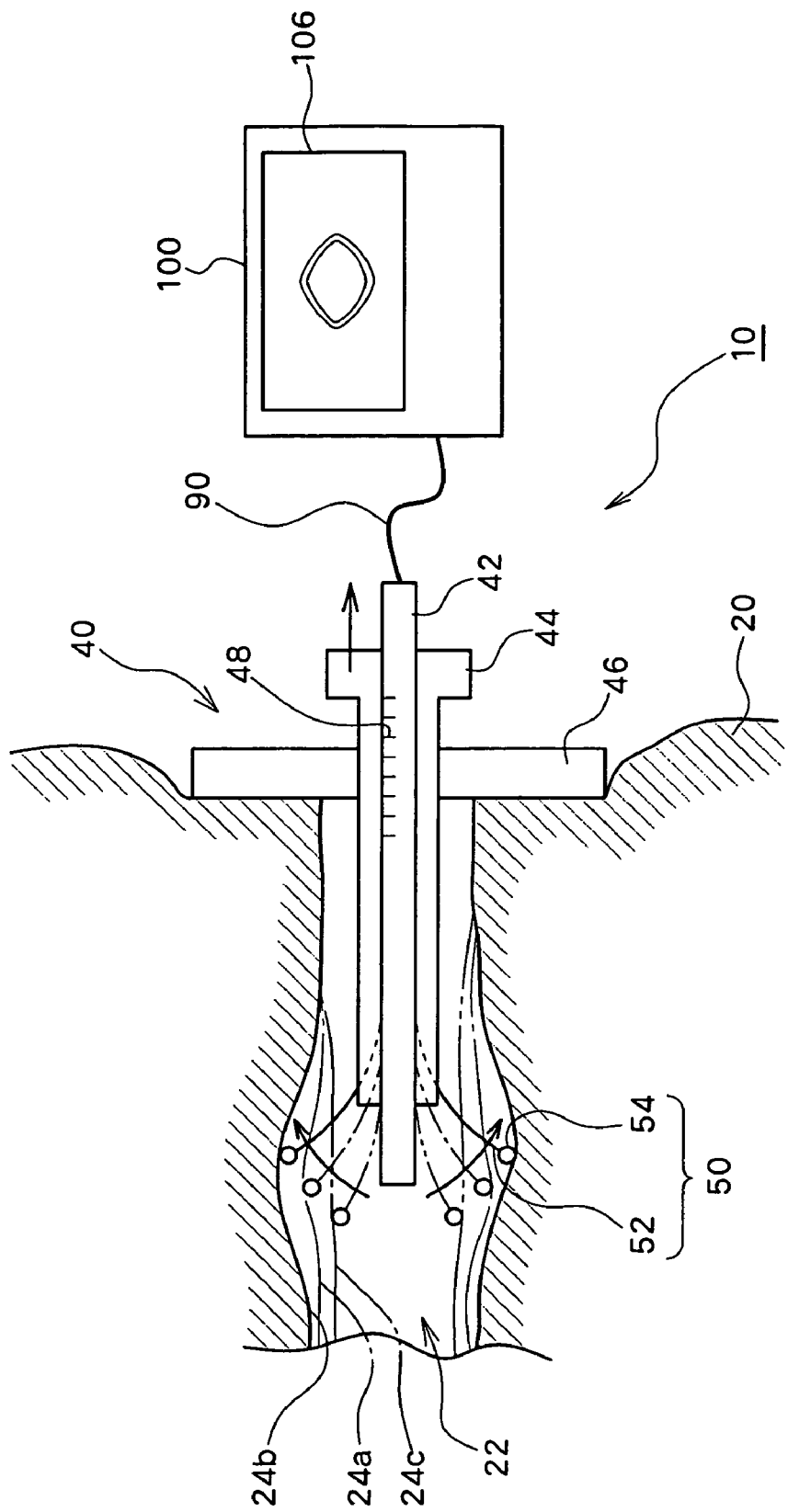
FIG. 1 is a schematic diagram showing a device for measuring elastic properties according to an embodiment of the present invention.

FIG. 1 is a drawing showing a configuration of a device for measuring elastic properties 10. The device for measuring elastic properties 10 is inserted into a vagina 22 of a living body (a patient) 20, and is also configured by comprising a probe part 40 for detecting a signal with respect to elastic properties of a living tissue of an inner wall 24 of the vagina 22, a signal cable 90, and a main part 100 of the device for processing and displaying the signal detected by the probe 40.

The probe 40 comprises a probe base 42, four probes 50 attached towards the tip end of the probe base 42, a sleeve 44 slidably fitted into an outer periphery of the probe base 42, and a flange plate 46 which is for guiding an outer periphery of the sleeve 44 and is to be applied to a vaginal introitus.

The probe base 42 is a rod-like member measuring several millimeters per side or in diameter. Signal lines from respective four probes 50 are housed within the probe base 42, and the signal lines extend out of a rear end portion of the probe base 42 toward the outside so as to be connected to the signal cable 90. An outer periphery of a rear end side of the probe base 42 is divided by scale marks 48 which represent the insertion depth of the probe base into the vagina 22 with respect to the flange plate 46.

Figure 2:
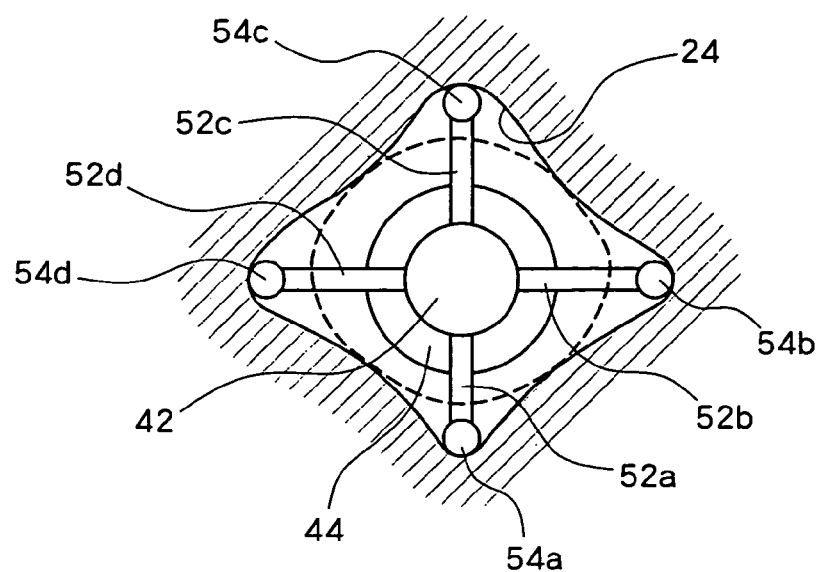
FIG. 2 shows the tip end of a probe part of a device according to the present invention, as viewed from inside a vagina.

Each of the respective probes 50 comprises a leaf spring 52, one end of which is attached to the probe base 42, and a sensor part 54 provided on a free end of the leaf spring 52. One end of each of the respective leaf springs 52 is provided at the same insertion depth in a direction of an axis of the probe base 42 such that these springs are symmetrically placed at intervals of 90° around the outer periphery of the probe base 42. FIG. 2 is a drawing of the tip of the probe part as viewed from a deep portion of the vagina. As shown in FIG. 2, four sensor parts 54a to 54d provided at free ends of four leaf springs 52a to 52d are placed at intervals of 90° around the insertion axis of the probe part and, therefore, can contact the tissue of the inner wall 24 of the vagina at the same insertion depths because of the elastic force of respective leaf springs 52a to 52d.

Figure 3:
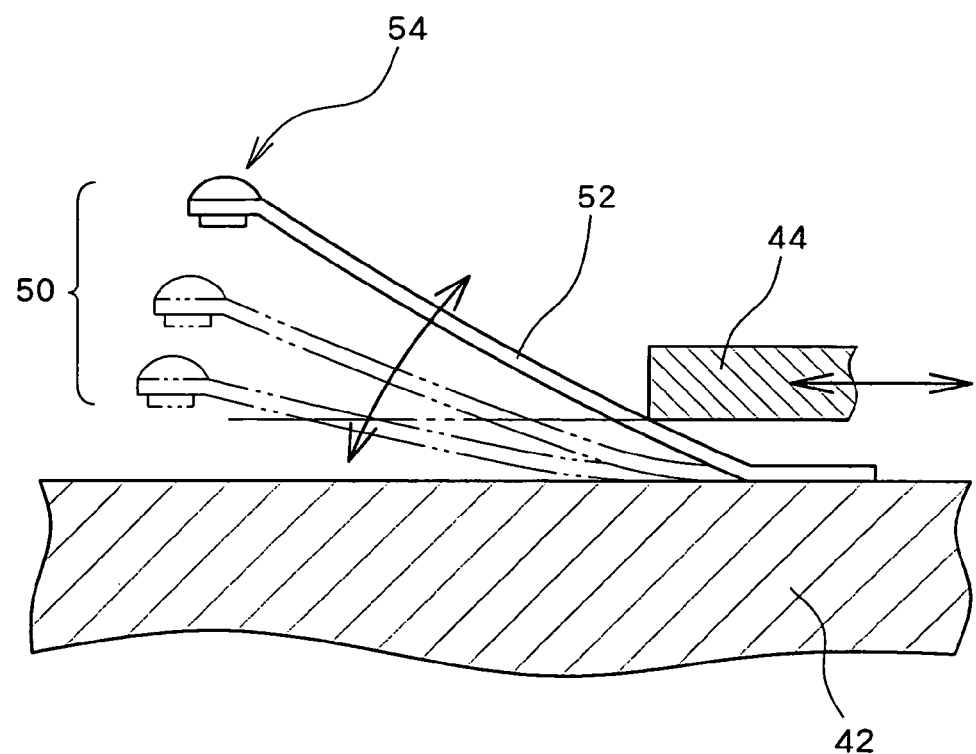
FIG. 3 is a drawing for illustrating a relationship among a probe base, a sleeve, and a probe in a device according to the present invention.

FIG. 3 is a drawing illustrating a relationship among the probe base 42, the sleeve 44, and the probe 50. When the sleeve 44 moves toward the left side of FIG. 3 with respect to the probe base 42, for example, the pipe-like inside of the sleeve 44 comes into contact with the leaf spring 52 of the probe 50, and when the sleeve 44 further moves toward the left side, the sleeve 44 acts so as to press the leaf spring 52 toward the probe base 42. Therefore, the sensor part 54 provided at the free end of the leaf spring 52 moves in a downward direction as the sleeve 44 moves toward the left side, and moves in an upward direction as the sleeve 44 moves toward the right side. In this way, the relative movement between the sleeve 44 and the probe part 42 allows the sensor part 54 provided at the free end of the leaf spring 52 to be driven in a manner of being pressed against and withdrawn from the tissue inside the vagina. The relative movement between the sleeve 44 and the probe base 42 can be achieved by a small-sized motor (not shown). Further, in simple measurement, the relative movement between the sleeve 44 and the probe base 42 can also be achieved by manual operation of an operator.

When the sleeve 44 moves toward the left side, the whole of the probe 50 including the sensor part 54 can also be housed within the sleeve 44. With such a configuration, the tip of the probe part 40 can be inserted to a predetermined depth in the vagina while the probe 50 having a complicated mechanism is housed within the sleeve 44, so that the insertion can be smoothly performed. Control of the insertion depth can be achieved by using the flange plate 46 and the scale marks ticked on the probe base 42. Then, by moving the sleeve 44 at the predetermined insertion depth, the four probes 50 can be opened and shut like an umbrella within the vagina. The number of probes is not limited to four, and two, three, or five or more probes may be used.

Figure 4:
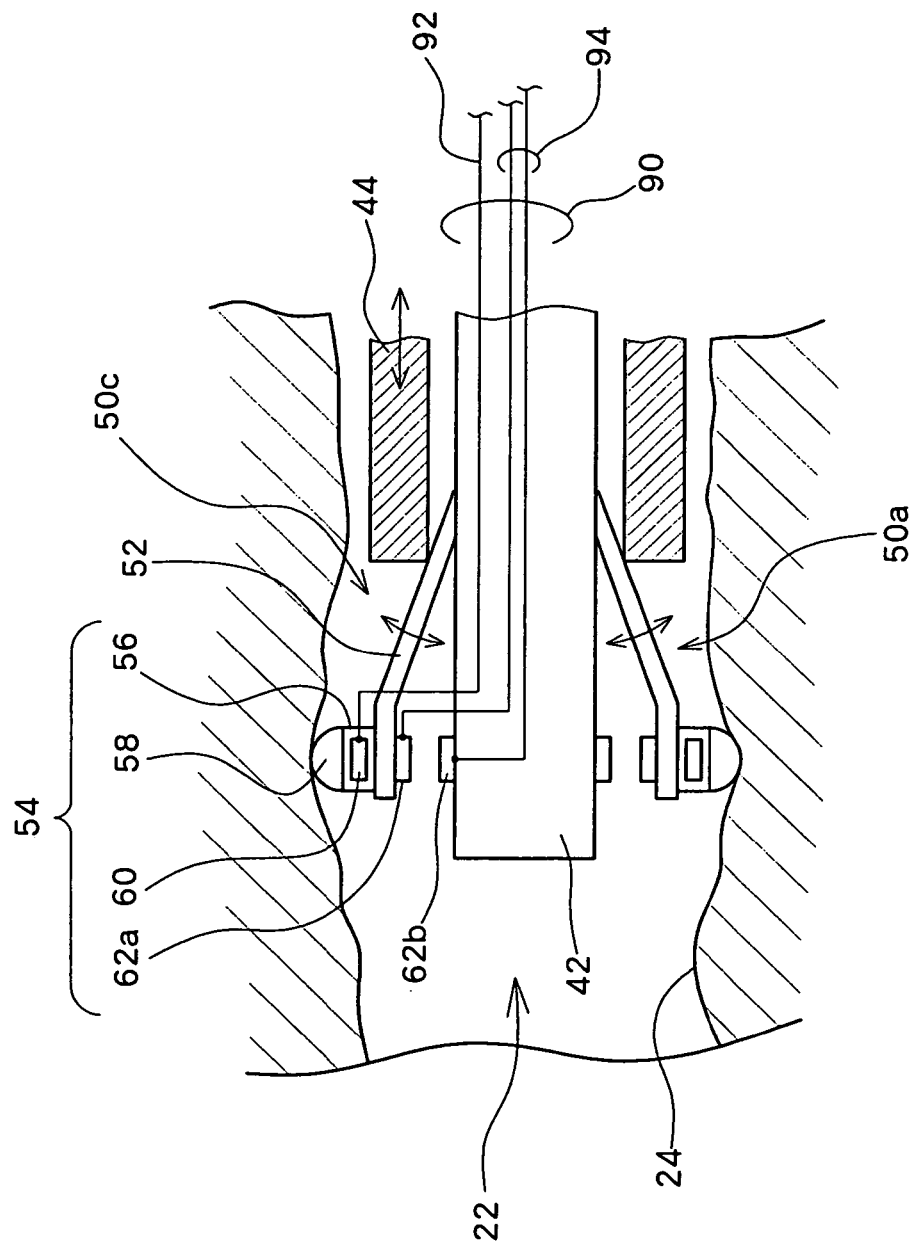
FIG. 4 is a detailed view of an area around a probe including a sensor part in a device according to the present invention.

FIG. 4 is a detail view around the probe 50 including the sensor part 54. The probe 50 is so formed that a generally semi-spherical plastic contact ball 58 having a stress detection base 56 is fitted to a free end of the leaf spring 52 attached to an outer periphery of the probe base 42, and a stress detection sensor 60 is adhered on the stress detection bases 56. A displacement detection sensor 62a is placed on one side of the leaf spring 52 opposite the side to which the stress detection base 56 is attached, and a displacement detection sensor 62b is placed on a surface of the probe base 42 facing to the displacement detection sensor 62a, such that these two sensors 62a and 62b are paired with each other. Signal lines 92 and 94 are connected to the stress detection sensor 60 and the displacement detection sensors 62a, 62b respectively, and introduced into a signal cable 90 passing through the probe base 42 as described above.

A strain gauge may be used as the stress detection sensor 60. A light-receiving element paired with a light-emitting element may be used as the displacement detection sensors 62a, 62b. Alternatively, other small-sized proximity sensors, such as a magnet paired with a magnetometric sensor, may also be used as the displacement detection sensor. The stress detection base 56 and the contact ball 58 may be made from the same material or may be made from different materials in a laminated structure.

Figure 5:
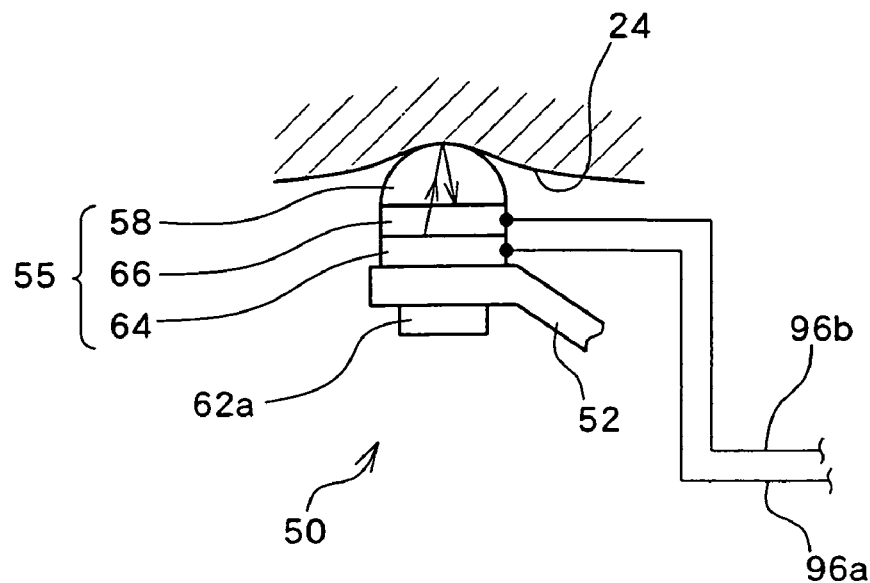
FIG. 5 is a segmentary view of a probe provided with a hardness sensor part in a device according to the present invention.

FIG. 5 is a segmentary view of the probe 50 provided with a hardness sensor part 55. Elements corresponding to those of the example of FIG. 4 are given the same reference numerals, and their detailed descriptions will not be repeated. The hardness sensor part 55 is so formed that a vibrator 64 and a vibration detection sensor 66 are laminated on a free end of the leaf spring 52 by using an adhesive or the like and a generally semi-spherical plastic contact ball 58 is adhesively attached to the laminate. In addition, a displacement detection sensor 62a and a displacement detection sensor 62b paired therewith are respectively placed on an opposite side of the leaf spring 52 and on a surface of the probe base 42 facing thereto, as illustrated in FIG. 4. Signal lines 96a and 96b are respectively connected to the vibrator 64 and the vibration detection sensor 66, and these signal lines 96a and 96b are introduced into a hardness detection part described below passing through the probe base 42 and via a signal cable 90 as described above.

The operation of the probe part 40 of the above described configuration will now be described. In a situation in which four probes 50 are shut like an umbrella so as to be housed within the sleeve 44, the probe part 42 and the sleeve 44 are inserted from an opening of the flange plate 46 to a certain insertion depth at which the elastic properties of the canal such as a vagina 22 of a patient are to be measured. Upon reaching the predetermined insertion depth, the sleeve 44 is gradually moved toward a proximal end (indicated by an arrow in FIG. 1) with respect to the probe base 42 by manual operation of the operator or by a small-sized motor, in any even such that the probes 50 open like an umbrella. At this point, the contact ball 58 moves toward the tissue inside the vagina 22, and then the contact ball 58 is pressed so as to dilate an inner wall of the vagina 22. Subsequently, the sleeve 44 is gradually returned toward the left side with respect to the probe base 42, and the probes 50 are gradually shut. At this point, the contact ball 58 moves away from the tissue inside the vagina 22, and then the contact ball 58 is returned in response to contraction of the inner wall of the vagina 22. For example, in FIG. 1, the position of an inner wall (24a, 24b, and 24c) of the vagina 22 will change from an inner wall 24a in an initial condition to an inner wall 24b in a dilatation condition, and to an inner wall 24c in a contraction condition, in response to pressing and releasing (withdrawing) motion of the contact ball 58.

A reaction force F caused by dilatation and contraction of the inner wall of the vagina 22 is detected by a stress detection sensor 60 provided on a stress detection base 56 to which the contact ball 58 is attached. If the stress detection sensor 60 is a strain gauge, the reaction force becomes a signal representing a change in resistance and is transmitted through the signal line 92 to a main part 100 of the device, where the signal is processed and calculated in terms of a stress.

On the other hand, a change in distance between the probe base 42 and the contact ball 58, that is, a relative displacement of dilatation and contraction of the inner wall of the vagina 22 caused by the contact ball 58 is detected by the displacement detection sensors 62a, 62b. That is, when a distance between the probe base 42 and the contact ball changes, a distance between the light-emitting element and the light-receiving element also changes. And corresponding to the change in distance, a signal which represents a change in light-receiving amount is generated and transmitted through the signal line 94 to the main part 100 of the device, where the signal is processed and calculated in terms of a displacement, for establishing an association with the previously determined stress.

Figure 6:
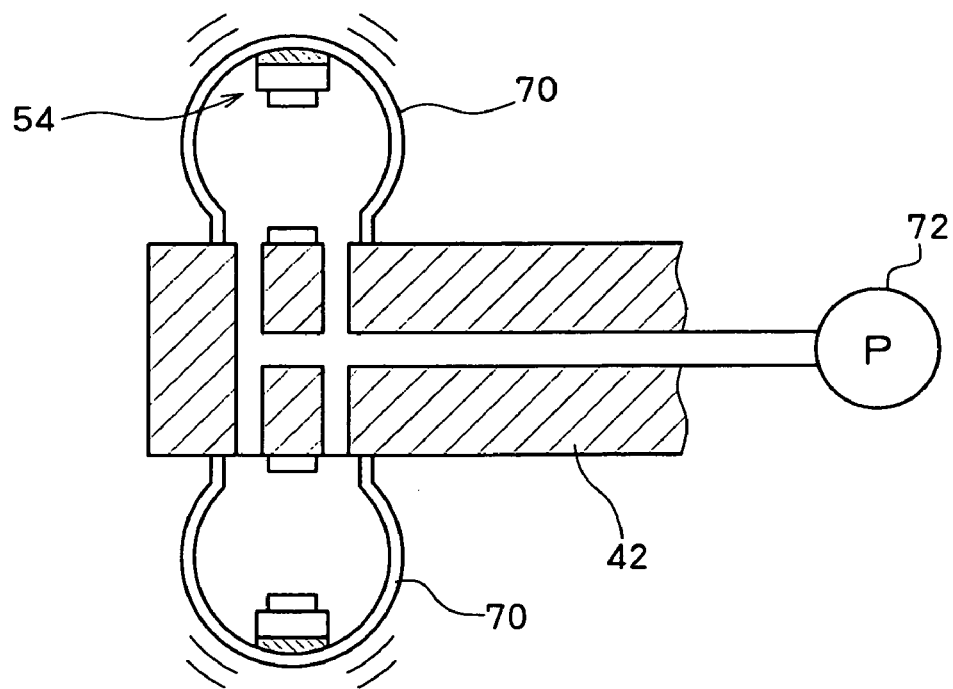
FIG. 6 is a drawing showing an example of a device according to the present invention which uses a balloon as a probe.

Another embodiment of the probe part will now be described. FIG. 6 shows an example in which the above-described leaf spring structure is replaced with a balloon which can be freely expanded and contracted in response to fluid pressure. In FIG. 6, a balloon 70 is attached to the probe base 42. An inner wall of the balloon 70 is provided with a probe 54. The balloon 70 is connected to a pump 72, and is driven so as to be pressed against and released from the tissue by adjusting the pressure of the pump 72.

Figure 7:
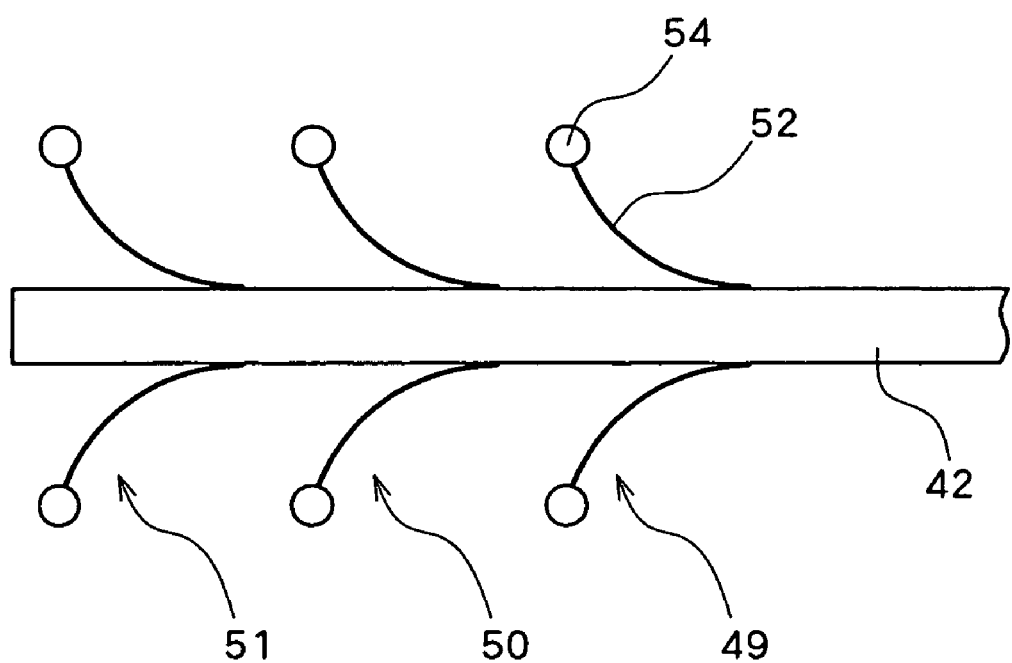
FIG. 7 is a drawing showing an example of a device according to the present invention in which four probes are provided at each of three different insertion depths.

FIG. 7 shows an example in which four probes 49, 50, and 51 are provided at each of three different insertion depths. With this configuration, a single sleeve can be used to gradually open the three sets of probes in increasing order of insertion depth and can also be used to gradually shut the probes in decreasing order of insertion depth. Three partial sleeves, which are respectively placed between the probe 51 and the probe 50, between the probe 50 and the probe 49, and at a proximal portion of the probe base with respect to the probe 49, may also be used to independently drive the respective probes 49, 50, and 51 to be pressed and released by providing a mechanism for individually and slidably moving these partial sleeves by remote control or the like. The insertion depth of the probe is not limited to the above described three levels, but may be set as appropriate depending on convenience in measurement.

Figure 8:
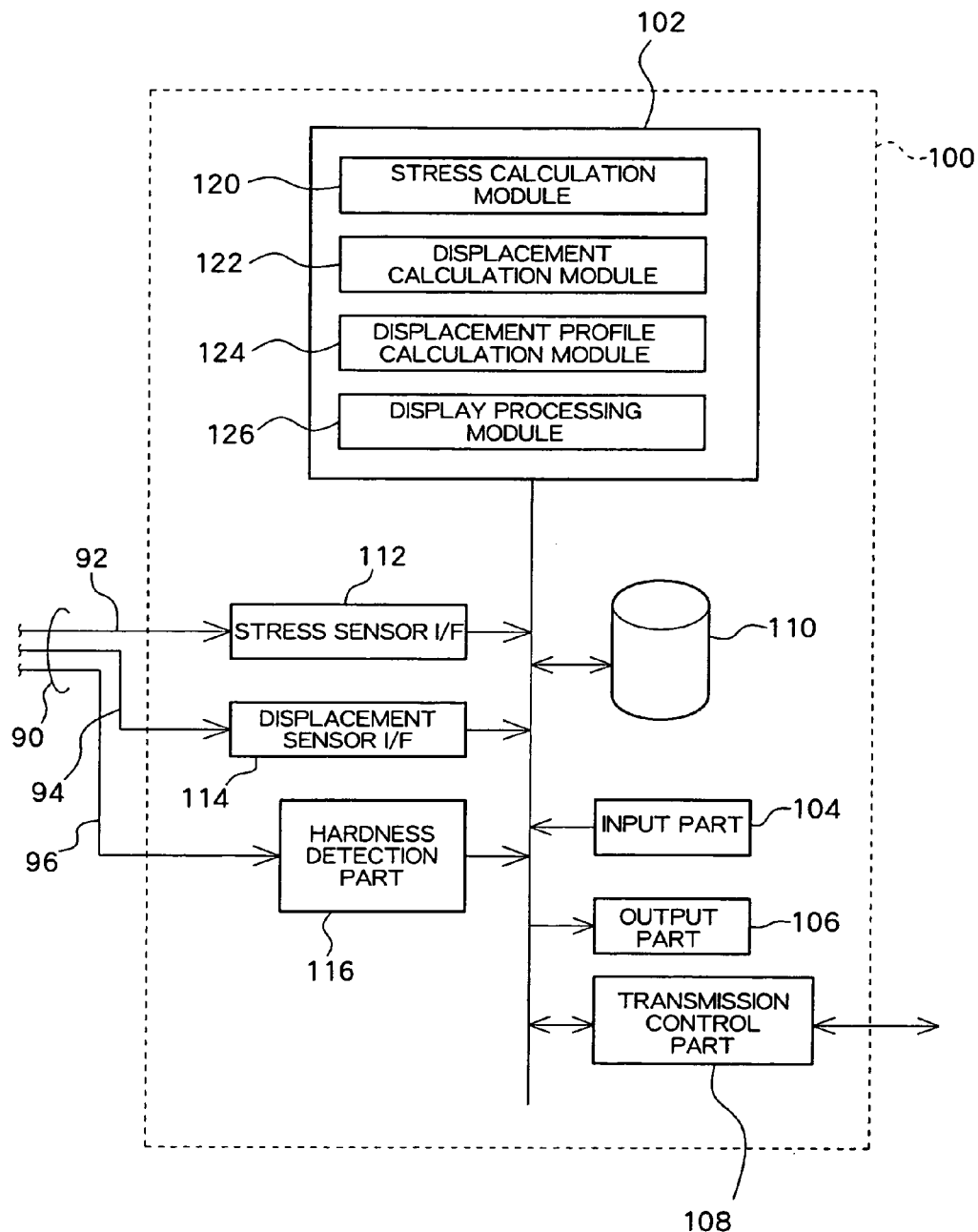
FIG. 8 is a block diagram of a main part of a device according to the present invention.

Next, a main part 100 of the device will be described. FIG. 8 is a block diagram of a main part 100 of the device. The main part of the device can be configured by additionally providing a common computer with an interface circuit substrate for stress measurement, an interface circuit substrate for displacement measurement, a hardness detection part circuit substrate for hardness measurement, and the like. The hardness detection part circuit substrate may also be configured as an independent device, to which a common computer is connected.

The main part 100 of the device comprises a CPU 102, an input part 104 such as a keyboard, an output part 106 such as a display, a transmission control part 108 connected via a network or the like to an external diagnostic device, and a storage device 110 in which data and the like calculated or generated by the CPU 102 are stored. The main part 100 of the device is also provided with a stress sensor I/F (InterFace) 112, a displacement sensor I/F 114, and a hardness detection part 116, connected to signal lines 92, 94, and 96, respectively. Each element of the main parts is connected with internal bus line.

The stress sensor I/F (InterFace) 112 in the above described example is a circuit which has a function of performing the conversion processing or the like for the purpose of digital signal processing on a change in resistance detected by the stress detection sensor 60. The displacement sensor I/F 114 is a circuit which has a function of performing the conversion processing or the like for the purpose of digital signal processing on a change in light-receiving amount detected by displacement detection sensors 62a, 62b.

Figure 9:
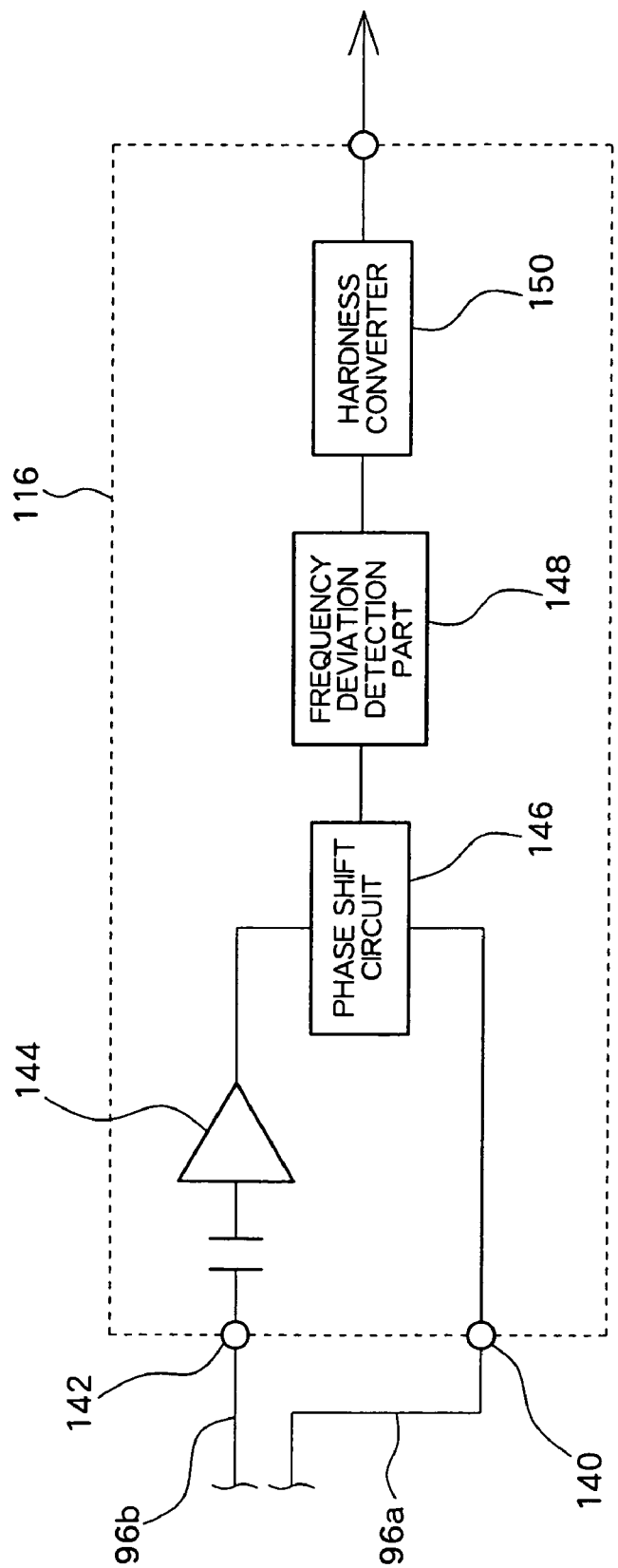
FIG. 9 is a block diagram of a hardness detection part in a device according to the present invention.

FIG. 9 is a block diagram of the hard detection part 116. The hard detection part 116 comprises an input terminal 140 connected to the vibrator 64 of the hard sensor part 55 via a signal line 96a and an output terminal 142 connected to the vibration detection sensor 66 via a signal line 96b. The hard detection part 116 also comprises an amplifier 144 whose input terminal is connected to the output terminal 142, and a phase shift circuit 146 provided between the output terminal of the amplifier 144 and the input terminal 140 so as to shift a phase difference to zero by modulating a frequency when the phase difference is produced between an input waveform to the vibrator 64 and an output waveform from the vibration detection sensor 66. Description of a phase shift circuit having the above described functions can be found in, for example, Japanese Patent Laid-Open Publication No. Hei 9-145691.

With the above described configuration, while a resonant state of a closed loop comprising the vibrator 64, the tissue, the vibration detection sensor 66, the amplifier 144, and the phase shift circuit 146 is maintained, any change in frequency resulting from a change in hardness of the tissue is detected by a frequency deviation detection part 148, and converted to a signal indicating the hardness by a hardness converter 150. The converted hardness signal is then converted to a digital signal. For conversion of the frequency change to the hardness, it is possible to use a conversion table or the like calibrated by a standard substance for example. In this way, a quantitative value for the hardness of the organism can be obtained.

Returning again to FIG. 8, a stress calculation module 120 has a calculation function such that a digital signal which represents a resistance change being input from the stress I/F 112 is subjected to the operational processing which utilizes a gauge factor of a stress gauge, for example, thereby converting a reaction force exerted on the contact ball at the tip of the probe into a digital value representing the stress on the living body tissue of the inner wall of the vagina.

A displacement calculation module 122 has a calculation function such that a digital signal which represents the change in the light-receiving amount input from the displacement sensor I/F 114 is subjected to the operational processing which utilizes a relational equation between a distance from a light-emitting element to a light-receiving element and a change in an light-receiving amount, thereby converting a moving amount of the contact ball at a tip of the probe into a digital value representing the displacement of the living body tissue of the inner wall of the vagina.

As described above, when the probe of the probe part is driven in a manner so as to be pressed against and withdrawn from the tissue, four stress detection signals and four displacement detection signals can be obtained from the four probes at the time point of each measurement, and, consequently, four stress values and four displacements are calculated from these signals. Each of thus calculated data can be stored in the storage device 110, with these data corresponding to the time point of measurement.

A displacement profile calculation module 124 has a function of calculating a displacement profile of an inner wall of the vagina by interpolation from four displacements obtained at the respective time point of measurement. A display processing module 126 has a function of performing processing such as the synthesizing of calculated stresses, displacement profiles, hardness and the like, and then outputting the display data on an output part 106. The calculated displacement profile and the generated display data can be stored in the storage device 110, with these profile and data corresponding to the time point of measurement.

A situation in which the displacement profile is determined by the displacement profile calculation module 124 and respective processing performed by the display processing module 126 will now be described below.

Figure 10:
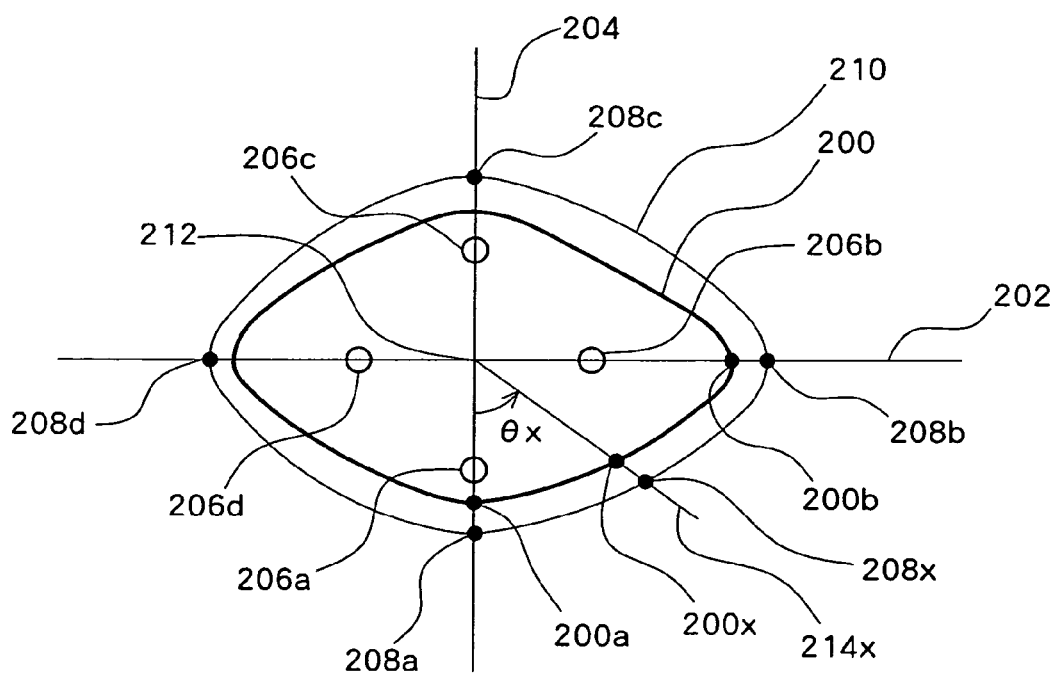
FIG. 10 is a schematic diagram showing a situation in which a displacement profile is calculated in a device according to the present invention.

FIG. 10 is a schematic diagram showing a situation in which the displacement profile is calculated. Because the four displacements determined by the displacement calculation module 122 are displacements at four measurement positions respectively provided at intervals of 90° around an insertion axis within the vagina, it is possible to obtain a profile of the overall inner wall of vagina at the insertion depth by interpolation between the adjacent measurement positions. As a standard reference for the interpolation, it is preferable to use a situation in which none of probes comes into contact with the inner wall of the vagina, that is, a standard profile of the inner wall of the vagina in which an inner wall stress of the vagina is not exerted. As the above described standard profile, it is possible to use a tomogram obtained by an X ray CT (Computed Tomography) method, a tomogram obtained by an MRI (nuclear Magnetic Resonance Imaging), and the like.

FIG. 10 shows a standard profile 200 at a predetermine depth within the vagina, to which the probe part is inserted within the vagina, and also shows four probe positions 206a to 206d which are obtained when the four probe positions are approximately aligned on a major axis 202 and a minor axis 204 of a cross section of the vagina. In this case, when the probes are pressed against the inner wall of the vagina by opening the probes like an umbrella, the above-described four probe positions move to respective positions 208a to 208d by respectively different amounts, because elastic properties of the living tissue at the inner wall of the vagina vary depending on their positions. A displacement profile 210 can be obtained by interpolation between the adjacent displacement measurement positions of four probe positions 208a to 208d such that the standard profile 200 is enlarged toward the outside while maintaining a geometrical approximately similarity.

In addition, a displacement profile can also be obtained by a method in which a point of intersection 212 of a major axis 202 and a minor axis 204 of the standard profile 200 is used as a reference point of interpolation and then a direction from the point of intersection 212 which is in a radial direction is interpolated. For example, a distance between the point of intersection 212 and the displacement measurement position 208a is compared with a distance between the point of intersection 212 and the position 200a on the minor axis of the standard profile 200 to determine a ratio $d_1$ thereof, and, similarly, a distance between the point of intersection 212 and the displacement measurement position 208b is compared with a distance between the point of intersection 212 and the position 200b on the major axis of the standard profile 200 to determine a ratio $d_2$ thereof. As for an area between the displacement measurement position 208a and the displacement measurement position 208b, a distance $L_o$ between a point of intersection 200x with the standard profile 200 and the point of intersection 212 is determined by drawing a line 214x from the point of intersection 212 in a radial direction at an angle of θx. An interpolation ratio dx is determined by proportionally allocating the ratios $d_1$ and $d_2$ depending on the magnitude of angle θx. A position of an interpolation point 208x can be determined by multiplying the interpolation ratio dx by the distance $L_0$. As described above, a displacement profile can be determined by the interpolation between the adjacent measurement positions.

Figure 11:
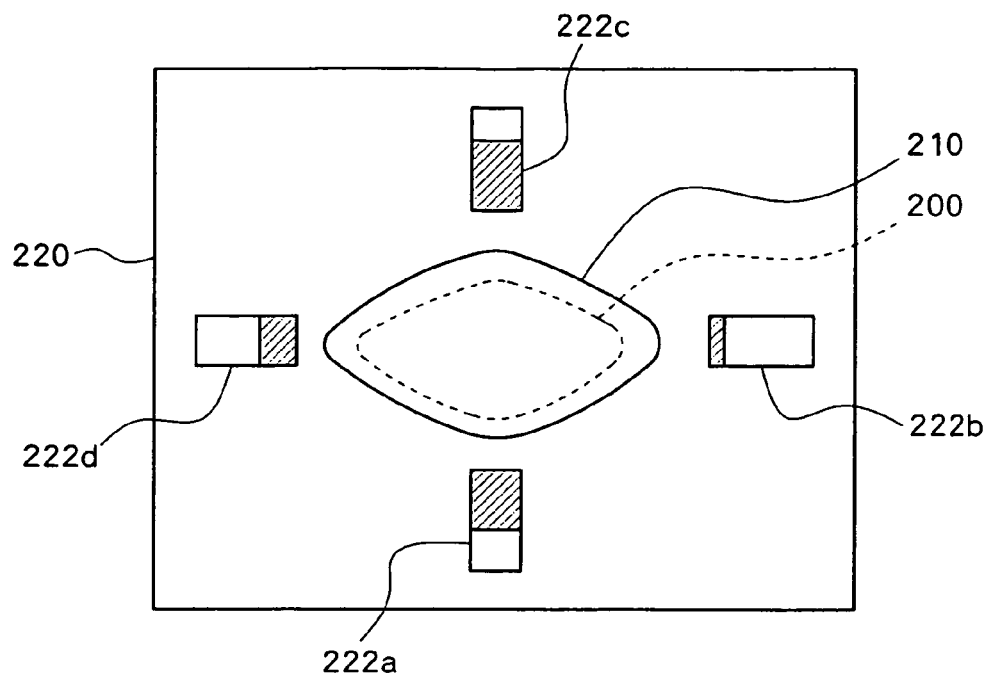
FIG. 11 is a drawing showing an example screen which displays displacement profile data in correspondence with stress data as displayed by a device according to the present invention.
Figure 12:
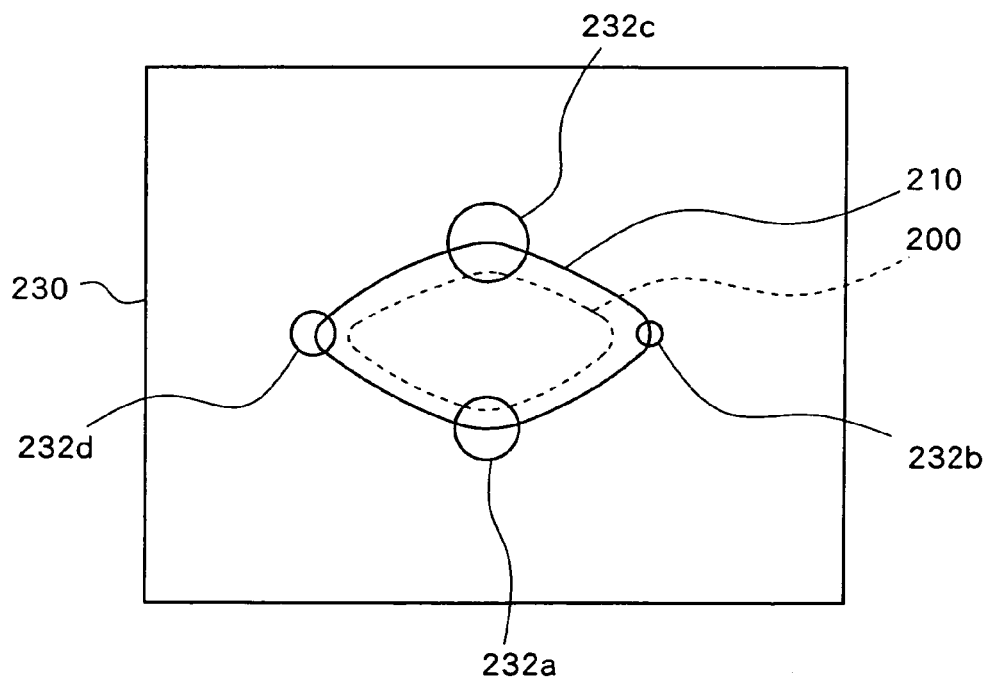
FIG. 12 is a drawing showing another example screen which displays displacement profile data in correspondence with stress data as displayed by a device according to the present invention.

FIGS. 11 and 12 show screens 220 and 230 respectively on which the displacement profile data corresponding to the stress data are displayed. The screens 220 and 230 are generated such that the stress data calculated by the stress calculation module 120 and the displacement profile data calculated by the displacement profile calculation module 124 are converted to the image data on a display processing module 126 and then subjected to the synthesizing processing.

On the screen 220 of FIG. 11, a displacement profile 210 is displayed with the standard profile 200, and stress values respectively corresponding to four probe displacements which are the basis for calculating the displacement profile 210 are displayed by four bar graphs 222a to 222d. Each of the bar graphs shows a calculated stress value as a diagonally shaded area within a frame of a full scale, which occupies a certain proportion of the full scale. Each of the bar graphs 222a to 222d are, on the margin of the screen 220, placed on a position corresponding to each of the four measurement positions on the displacement profile 210.

On the screen 230 of FIG. 12, four stress values are shown as circles 232a to 232d having diameters corresponding to the magnitudes of their respective stress values. Each of the circles 232a to 232d showing stress values is placed at a position corresponding to four measurement positions on the displacement profile 210.

Figure 13:
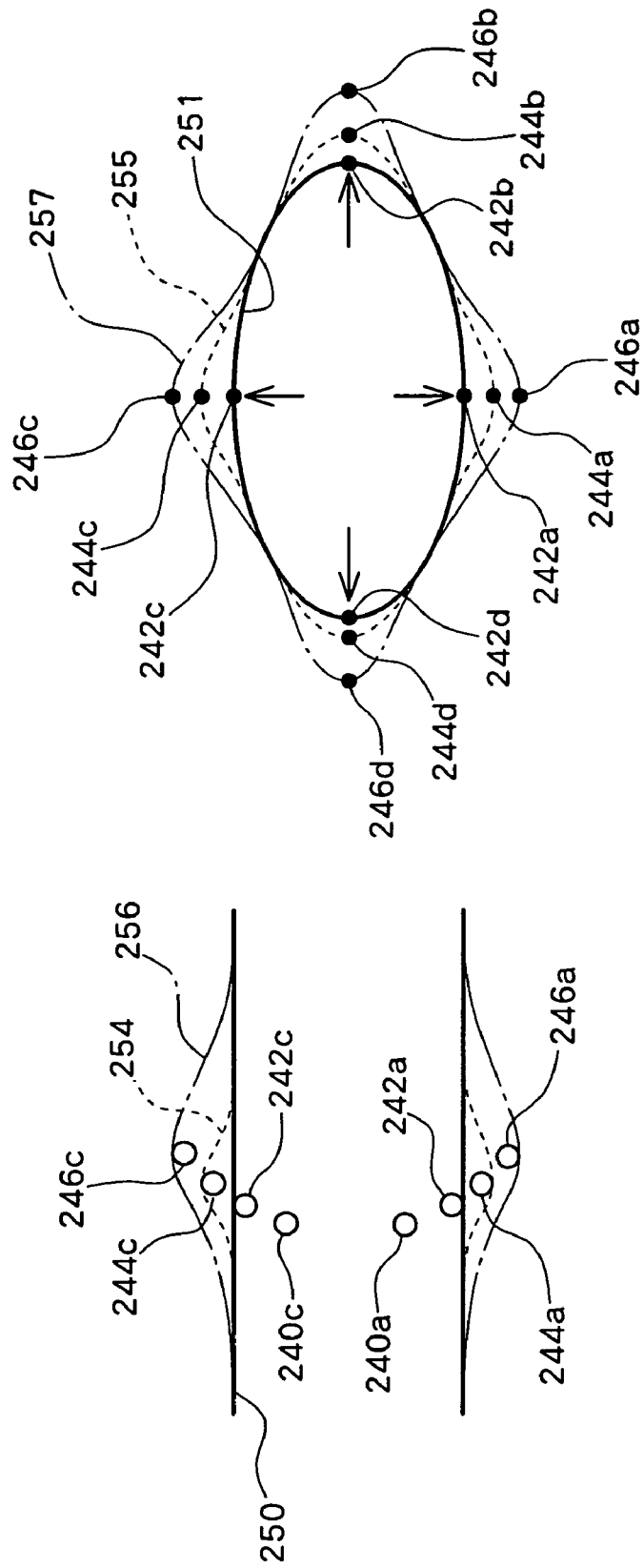
FIG. 13 is a drawing showing a situation in which a displacement profile is changing when a probe is pressed and withdrawn during an operation thereof in a device for measuring elastic properties of an embodiment according to the present invention.

FIG. 13 shows an example in which a displacement profile is continuously changing as a probe is pressed and released by an operation at the same insertion depth. FIG. 13(a) is a sectional view around the vagina sectioned by a plane parallel to an insertion axis of the probe, and (b) is a sectional view around the vagina sectioned by a plane perpendicular to the insertion axis. If the probes are not sufficiently opened, tip portions 240a to 240d do not come in contact with an inner wall 250 of the vagina. As the probes are gradually opened by operations, the tip portions 242a to 242d of the probes come in contact with the inner wall 250 of the vagina. Until this point, the inner wall of the vagina still has a standard profile 251. As the probes are further opened, the tip portions 244a to 244d of the probes stretch out the inner wall of the vagina. From positions of the tip portions 244a to 244d of the probes at this moment, a displacement profile 255 can be determined by the above described interpolation. Then, as the probes are still further opened, the tip portions 246a to 246d of the probes stretch out the inner wall of the vagina, and then a displacement profile 257 can be determined from positions of the tip portions 246a to 246d of the probes at this moment. Similarly, displacement profiles can be successively determined when the probes are gradually closed. As shown in FIG. 13(b), a change in elastic characteristics of the inner wall of the vagina can be visually displayed and easily understood from the display when each displacement profile at each measurement timing during the successive movements of the probes are displayed sequentially superimposed on the previously displayed profile in accordance with each measurement timing, rather than by displaying only a single displacement profile at each measurement timing.

Figure 14:
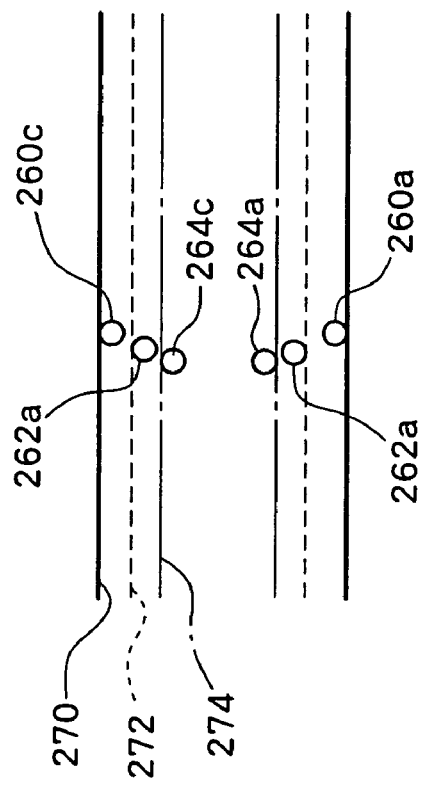
FIG. 14 is a schematically explaining drawing showing a situation in which a displacement profile is changing when a probe is pressed and withdrawn only by movements of an inner wall of a vagina in a device for measuring elastic properties of an embodiment according to the present invention.
Figure 14:
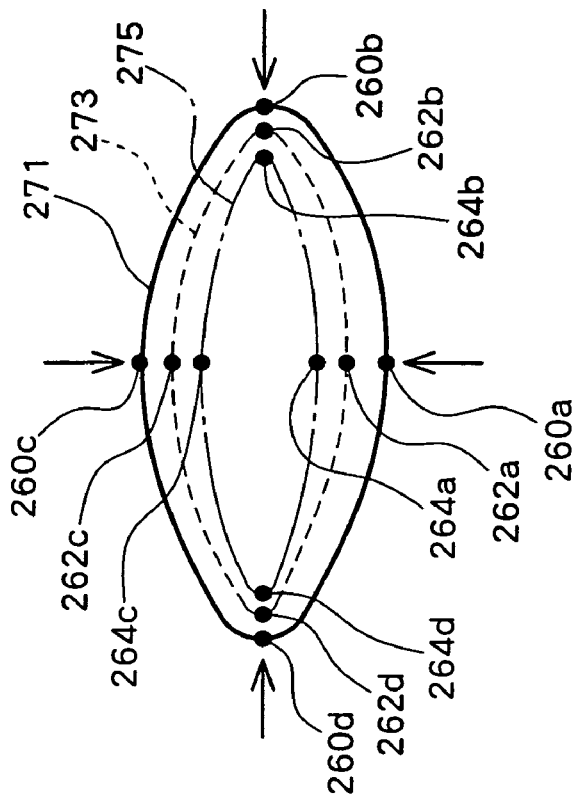

FIG. 14 shows a situation in which a displacement profile is continuously changing when the probes are freed from a sleeve at the same insertion depth, that is, when the probes are pressed and released only by a movement of the inner wall of the vagina. Details of FIG. 14(a), (b) are the same as FIG. 13. When a probe part is inserted into the vagina of a patient and then a sleeve is sufficiently returned toward an operator, tip portions 260a to 260d of the probes come in contact with the inner wall 270 of the vagina. At this moment, the inner wall of the vagina still has a standard profile 271. If the patient "overstrains" under such conditions, an inner wall 272 of the vagina is contracted and further tip portions 262a to 262d are pushed back in response to the contraction, therefore, a displacement profile 273 can be determined from positions of the tip portions 262a to 262d of the probes at this moment. If the patient further "overstrains", an inner wall 274 of the vagina is contracted and further tip portions 264a to 264d are pushed back in response to the contraction, therefore, a displacement profile 275 can be determined from positions of the tip portions 264a to 264d of the probes at this moment. Similarly, displacement profiles can be successively determined when the patient relaxes.

It is possible to easily understand the elastic characteristics of the inner wall of the vagina when each displacement profile at each measurement timing during the successive "overstraining" and "relaxing" efforts made by a patient are displayed sequentially superimposed on the previously displayed profile in accordance with each measurement timing, rather than by displaying only a single displacement profile at each measurement timing. This method clearly reflects a degree of elasticity recovery of muscles which support an urethra for the purpose of preventing urinary incontinence. Although the tissue of the inner wall of vagina is practically pushed back by resiliency of the leaf spring of the probe, a movement of the tip portion of the probe has been considered, for simplifying the explanation, to be created only by a movement of the inner wall of vagina caused by the "overstraining".

Figure 15:
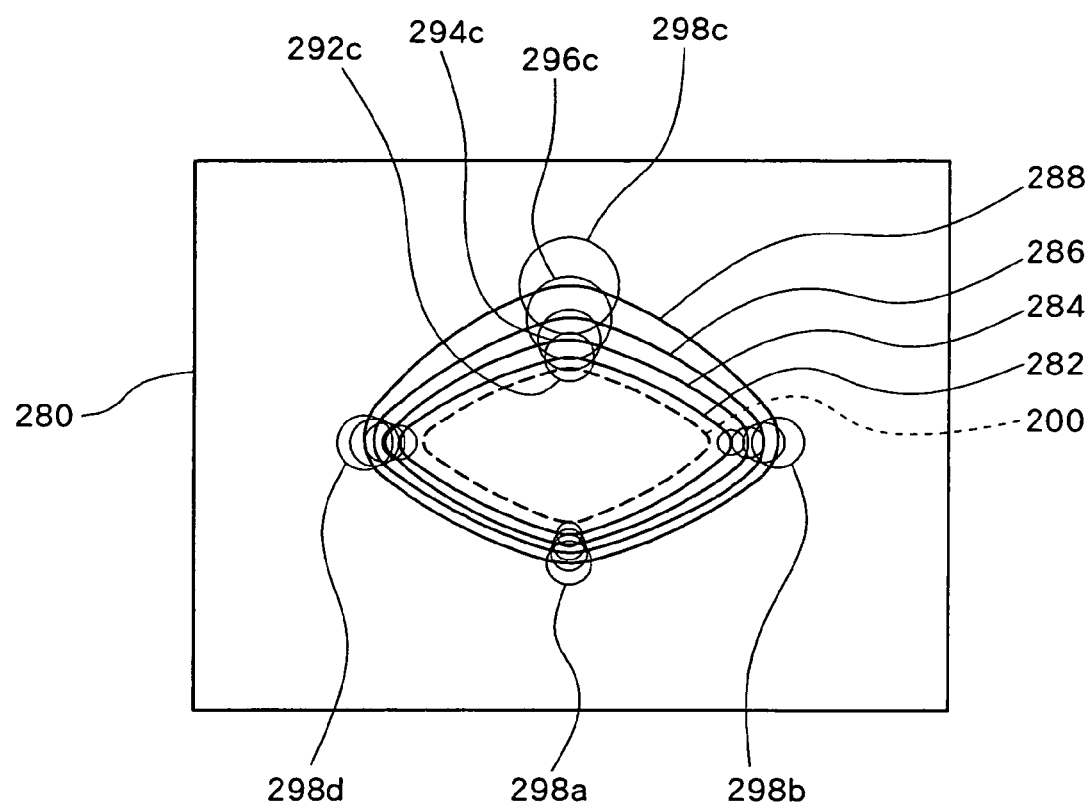
FIG. 15 is a drawing showing another example of a display screen which displays sets of a displacement profile and a circle representing a stress such that the displacement profile is superimposed on the circle at each time point of measurement performed in a device according to the present invention.

FIG. 15 shows a screen 280, on which all of displacement profiles 282 to 288 at respective measurement timings correlated with circles 292 to 298 representing stresses are superimposed on each other. It may also be possible to emphasize a certain displacement profile and a stress depending on the difference in measurement timings. For example, the color of a line representing a certain displacement profile and a certain circle of stress at a certain measurement timing can be varied compared with other profiles and circles at other measurement timings. Various types of lines may also be used on a single screen.

The screen 280 is generated such that the stress data and the displacement profile data at respective measurement timings stored in the storage device 110 are converted to the image data by a display processing module 126 and then subjected to the synthesizing processing. In addition, stress data calculated by the stress calculation module 120 and displacement data calculated by the displacement calculation module 122 at respective measurement timings are converted to the image data on a display processing module 126 in real time, and then are sequentially subjected to the synthesizing processing to obtain the above described screen, wherein each displacement profile and each circle representing a stress are sequentially superimposed on the previously displayed profiles and circles as a certain measurement timing shifts toward a next measurement timing.

Figure 16:
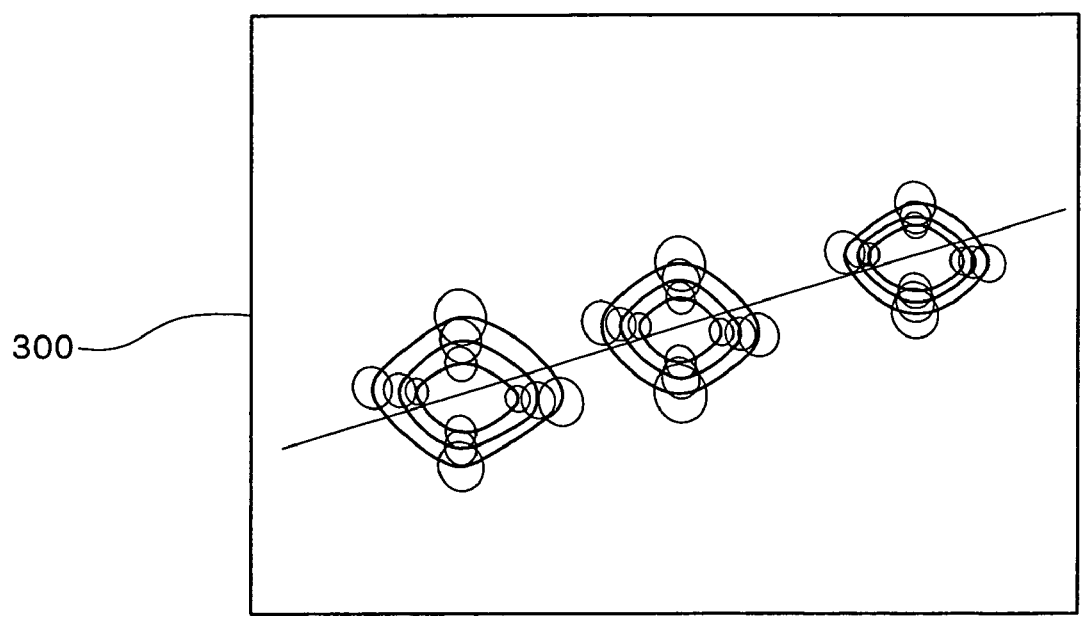
FIG. 16 is a drawing showing an example display screen which displays sets of a displacement profile and a circle representing a stress such that the displacement profile is superimposed on the circle at each time point of measurement performed at each of three insertion depths in a device according to the present invention.

FIG. 16 shows a screen 300 on which displacement profiles and circles representing stresses at respective measurement timings are superimposed on each other at each of three insertion depths. As shown in FIG. 16, graphics at respective measurement timings are obliquely placed on the screen for the purpose of clearly showing these graphics. In this way, it is also possible to clearly display in real time not only a change in displacement profile and stress around an inner periphery, but also a change in displacement profile and stress in a depth direction of the inner wall of the vagina.

The screens 220, 230, 280, and 300 of FIGS. 11, 12 and FIGS. 15, 16 are displayed by an output part 106 of a main part 100 of the device. In addition, data which constitute these screens can be transmitted to an external diagnostic device via a transmission control part 108 of the main part 100 of the device or through a communication cable or a radio network. For example, a complete set of a device for measuring elastic properties of a living tissue 10 is installed in a patient's home, such that the patient can perform measurement themselves, and can observe a monitor screen which is an output part 106 of a main part 100 of the device while simultaneously transmitting the data to their doctor while their doctor simultaneously observes the same screen. Therefore, the patient can evaluate a degree of effect of an elastic recovery training in real time by themselves at home, while their doctor simultaneously diagnoses their condition, while observing the data simultaneously. This enables the physician to instantly issued a prescription or instructions to the patient.

Although an example manner of displaying stress data corresponding to displacement profiles has been described in reference to FIGS. 11, 12, 15, and 16, other manners of display are possible, such as, for example, display of hardness data, in place of or with the stress data, corresponding to the displacement profiles.

INDUSTRIAL APPLICABILITY

As has been described above, a device for measuring elastic properties of a living tissue according to the present invention is suitable for evaluating the elasticity of tissue, such as muscle tissue, for the purpose of properly performing surgery or for evaluating a degree of elasticity recovery of the tissue after surgery, for example.

The invention claimed is:

1. A device for measuring elastic properties of a living tissue, wherein elastic properties of a tissue surrounding a canal of a living body are measured by inserting the device through the canal, the device comprising:
   a probe base to be inserted through the canal;
   a sleeve slidably fitted into an outer periphery of the probe base;
   a plurality of probes provided around an insertion axis of the probe base and having an end attached to the probe base at a same insertion depth in a direction of the insertion axis, the plurality of probes being placed in close vicinity to the tissue inside the canal, each of the plurality of probes comprising:
      a leaf spring, one end of which is attached to the probe base, wherein a relative movement between the sleeve and the probe base allows a free end of the leaf spring to be driven in a manner of being pressed against and withdrawn from the muscle tissue surrounding the canal with an elastic force of the leaf spring from a plurality of measurement positions on the tissue, the free end of the probe being opposite the attached end in the direction of insertion;
      a generally semi-spherical contact ball having a stress detection sensor that detects a stress applied to the tissue at at least one of the measurement positions on the basis of a reaction force from the tissue, the generally semi-spherical contact ball being disposed at a distal most tip of the free end of the leaf spring on a side of the probe facing the tissue; and
      a displacement detection sensor in the form of a proximity sensor that detects a displacement of the tissue at the at least one of the measurement positions on the basis of a displacement of the stress detection sensor radially from the probe base, an element of the proximity sensor being disposed at the distal most tip of the free end of the leaf spring on a side of the probe opposite the stress detection sensor and displaced from the probe base; and
   a displacement profile calculation part for calculating a displacement profile of the canal displaced in a manner so as to be pressed and withdrawn, based on each displacement at each measurement position and on a standard profile having no stress applied to the tissue, at the above described insertion depth into the canal; and
   display means for displaying a change of the displacement profile caused by the pressing and withdrawing motions and a change of each stress value corresponding to each profile in real time.

2. The device for measuring elastic properties of a living tissue according to claim 1, wherein the standard profile is a tomogram at the insertion depth into the canal.

3. The device for measuring elastic properties of a living tissue according to claim 1, wherein the display means displays the displacement profile, and further displays each graphic of a size corresponding to each value of the stress at the each measurement position so as to be superimposed on a position corresponding to the each measurement position on the displacement profile.

4. The device for measuring elastic properties of a living tissue according to claim 2, wherein the displacement profile calculation part calculates a displacement profile by interpolation between adjacent measurement positions, based on the each displacements at the each measurement position.

5. The device for measuring elastic properties of a living tissue according to claim 1, wherein separate pluralities of probes are provided at each of a plurality of insertion depths.

6. The device for measuring elastic properties of a living tissue according to claim 1, further comprising storage means for storing displacement profiles at respective measurement times and stress values corresponding to the profiles,
   wherein the display means read out the displacement profiles and the respective stress values corresponding to the profiles at the respective measurement times from the storage means in order to display the profiles and the stress values, respectively.

7. The device for measuring elastic properties of a living tissue according to claim 1, further comprising transmission means for externally transmitting the displacement profiles at the respective measurement times and the respective stress values corresponding to the profiles.

8. The device for measuring elastic properties of a living tissue according to claim 1, wherein the proximity sensor comprises two elements, a first element being disposed at the distal most tip of the free end of the leaf spring on a side of the probe opposite the stress detection sensor and a second element being disposed on the probe base facing the first element.

9. A device for measuring elastic properties of a living tissue, wherein elastic properties of a tissue surrounding a canal of a living body are measured by inserting the device through the canal, the device comprising:
   a probe base to be inserted through the canal;
   a sleeve slidably fitted into an outer periphery of the probe base;
   a plurality of probes provided around an insertion axis of the probe base and having an end attached to the probe base at a same insertion depth in a direction of the insertion axis, the plurality of probes being placed in close vicinity to the tissue inside the canal, each of the plurality of probes comprising:
      a leaf spring, one end of which is attached to the probe base, wherein a relative movement between the sleeve and the probe base allows a free end of the leaf spring to be driven in a manner of being pressed against and withdrawn from the muscle tissue surrounding the canal with an elastic force of the leaf spring from a plurality of measurement positions on the tissue, the free end of the probe being opposite the attached end in the direction of insertion;

a generally semi-spherical contact ball having hardness sensor part, the generally semi-spherical ball being disposed at a distal most tip of a free end of the leaf spring on a side of the probe facing the tissue, the free end of the probe being opposite the attached end of the probe in the direction of insertion;

hardness detection means for detecting a hardness of the tissue at at least one of the measurement positions on the basis of a signal from the hardness sensor part;

a displacement detection sensor in the form of a proximity sensor that detects a displacement of the tissue at the at least one of the measurement positions on the basis of a displacement of the hardness sensor part radially from the probe base, an element of the proximity sensor being disposed at the distal most tip of the free end of the leaf spring on a side of the probe opposite the hardness sensor part and displaced from the probe base;

a displacement profile calculation part for calculating a displacement profile of the canal displaced in a manner so as to be pressed and withdrawn, based on each displacement at each measurement position and on a standard profile having no stress applied to the tissue, at the insertion depth into the canal; and display means for displaying a change of the displacement profile caused by the pressing and withdrawing motion and a change of each hardness corresponding to the profile in real time.

10. The device for measuring elastic properties of a living tissue according to claim 9, wherein:

the hardness sensor part comprises a vibrator, a vibration detection sensor, an input terminal connected to the vibrator, and an output terminal connected to the vibration detection sensor; and the hardness detection means comprises an amplifier whose input terminal is connected to the output terminal of the hardness sensor part and a phase shift circuit provided between the output terminal of the amplifier and the input terminal of the hardness sensor part so as to shift a phase difference to zero by modulating a frequency when the phase difference is produced between an input waveform to the vibrator and an output waveform from the vibration detection sensor, the hardness of the tissue being detected from a change of the frequency that is caused by a change in hardness of the tissue while keeping a resonant condition of a closed loop comprising the hardness sensor part and the tissue.

11. The device for measuring elastic properties of a living tissue according to claim 9, wherein the proximity sensor comprises two elements, a first element being disposed at the distal most tip of the free end of the leaf spring on a side of the probe opposite the hardness sensor part and a second element being disposed on the probe base facing the first element.

12. The device for measuring elastic properties of a living tissue according to claim 9, wherein the proximity sensor comprises a light emitting or receiving element.

* * * * *